(12) United States Patent
Cope et al.

(10) Patent No.: US 6,397,782 B1
(45) Date of Patent: Jun. 4, 2002

(54) BUTTERFLY REARING KIT

(76) Inventors: Eric S. Cope; Susan S. Cope, both of 510 Harbison Ave., National City, CA (US) 91950

( * ) Notice: Subject to any disclaimer, the term of this patent is extended or adjusted under 35 U.S.C. 154(b) by 0 days.

(21) Appl. No.: 09/567,391

(22) Filed: May 9, 2000

(51) Int. Cl.[7] .......................... A01K 1/03; A01K 31/06
(52) U.S. Cl. ....................... 119/452; 119/475; 119/416
(58) Field of Search ............................ 119/416, 475, 119/452, 463, 707, 6.5, 6.6

(56) References Cited

U.S. PATENT DOCUMENTS

| | | | | |
|---|---|---|---|---|
| 4,250,833 A | * | 2/1981 | Waldon | 119/6.5 |
| 4,282,829 A | * | 8/1981 | Tweed | 119/6.5 |
| 5,002,013 A | * | 3/1991 | Brown | 119/6.5 |
| 5,377,617 A | * | 1/1995 | Harwich | 119/6.5 |
| 5,799,611 A | * | 9/1998 | Park | 119/248 |
| 6,223,690 B1 | * | 5/2001 | Park | 119/248 |

* cited by examiner

Primary Examiner—Charles T. Jordan
Assistant Examiner—Judith A. Nelson
(74) Attorney, Agent, or Firm—Donn K. Harms

(57) ABSTRACT

A butterfly rearing kit including an enclosure in which metamorphosis of a butterfly larva or butterfly chrysalis into a butterfly can be carried out. Basically, the kit includes first and second transparent plastic domes having open bases that can be releasably fastened together to form an enclosure. The enclosure may be supported by a third dome secured to the enclosure with the open base extending downwardly or on a rod extending out through said second dome. In one embodiment, a cup is provided for a butterfly larva with a cap to which the larva attaches the hanging chrysalis. The cap can be removed from the cup and placed over an opening in the top of the enclosure, so that final metamorphosis to a butterfly occurs in the enclosure. The kit preferably includes a moss like material along the bottom of the enclosure and butterfly larva food where the process starts with a larva. In a second embodiment, a chrysalis is secured to a cap which is placed over an enclosure opening with the chrysalis extending into the enclosure to complete metamorphosis.

19 Claims, 2 Drawing Sheets

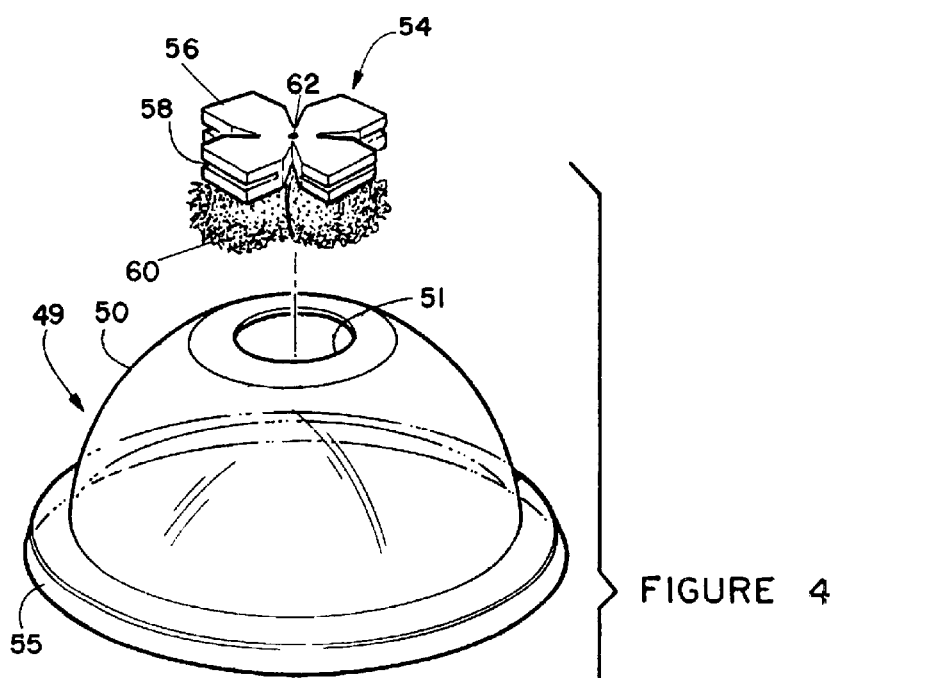
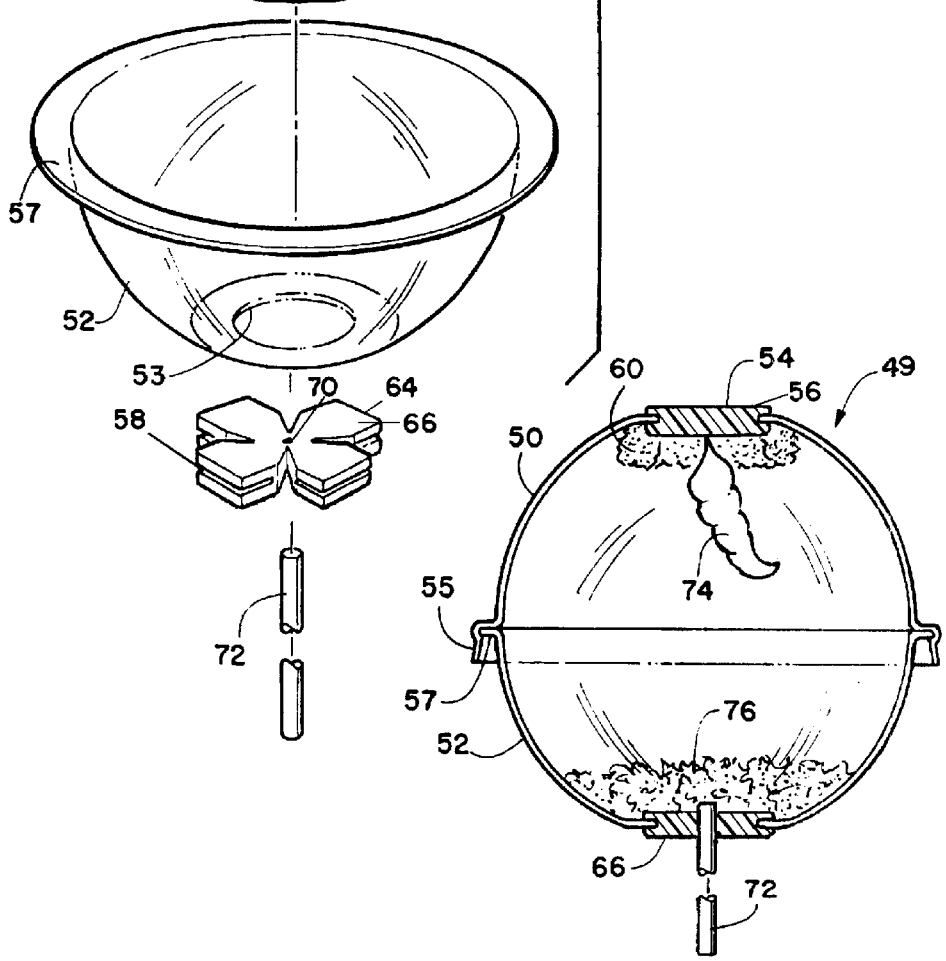
FIGURE 4
FIGURE 5

BUTTERFLY REARING KIT

FIELD OF THE INVENTION

This invention relates to enclosures for housing a butterfly larva or butterfly chrysalis during metamorphosis into a butterfly.

BACKGROUND OF THE INVENTION

Observing a butterfly larva form a chrysalis and then seeing a butterfly emerge from the chrysalis is both interesting and educational. A number of butterfly rearing kits have been developed and marketed, both as gifts for a person and for use in school science projects. Generally, the kits include a container in the form of a tent or cardboard box with a thin plastic sheet window for seeing into the container. An arrangement for allowing the chrysalis to hang freely is ordinarily included, together with a butterfly larva or a chrysalis. Usually a day or two after the butterfly emerges and extends its wings the butterfly is released into the environment.

There are a number of restrictions on the release of butterflies, to prevent non-native butterflies from being released and crowding out butterflies that are native to an area. In general, free release of Painted Lady and Monarch butterflies is permitted throughout the United States.

While the box-like rearing containers are effective, they tend to be dark inside with few windows though which light can enter. Observing the metamorphic process is difficult with these prior containers. Many are unfolded from cardstock and are relatively flimsy, potentially coming apart during transportation by a child, such as between home and school. The basically unattractive appearance of many prior rearing containers tends decrease the interest of children.

Food for butterfly larva, if provided, is not arranged in a way convenient to the larva. A convenient, effective, material that the larva may use for hanging the chrysalis in imitation of natural conditions enjoyed by wild larva is not always provided.

Thus, there is a continuing need for improved butterfly rearing containers, that are relatively sturdy, that permit easy observation, that allow light to easily enter and that are very attractive in appearance.

SUMMARY OF THE INVENTION

The above-noted problems, and others, are overcome by the butterfly rearing kit of this invention, which basically comprises two generally similar concave transparent plastic open-based domes, means for releasably securing the bases of the two domes together to form an approximately spherical enclosure, a small opening in the first dome, a cover for the opening, means for supporting a fibrous material surrounding the opening and support structure engaging the second dome for supporting the enclosure with the opening approximately uppermost.

While any suitable arrangement for connecting the first and second domes together, an optimum arrangement that is both easily connected and disconnected and is highly resistant to failure includes an outwardly extending flange on the base of each first and second dome, the flange on the first dome having an outer rim extending away from the dome. The second dome flange is sized to fit tightly inside the rim on the first dome.

Preferably, the first dome rim has an inwardly projecting line or as linear series of small projections extending towards the inside so that the second dome flange "snaps" past the projections to be held in place. The enclosure can be opened by pulling the two domes apart, so that the flange "snaps" outwardly over the projections. This is a simple, effective and durable connection arrangement.

Where a butterfly larva is placed in the enclosure to form the chrysalis and, eventually, a butterfly, larva food is preferably included in the enclosure. Where a butterfly chrysalis is to be placed in the enclosure, preferably the chrysalis is secured to the fibrous material by a glue such as a low temperature hot glue supplied by a glue gun to hang downwardly toward the center of the enclosure.

Any suitable support means may be provided to support the enclosure in the desired orientation. Typically, a wide base may be secured to the enclosure, an elongated thin stick may be secured to the second dome to permit the enclosure to be held above a vase-like housing or inserted in dirt in a pot or the like, etc.

BRIEF DESCRIPTION OF THE DRAWING

Details of the invention, and of preferred embodiments thereof, will be further understood upon reference to the drawing, wherein:

FIG. 4 is an exploded view of a second embodiment of the butterfly rearing kit; and FIG. 5 is a vertical section through the second embodiment.

DETAILED DESCRIPTION OF PREFERRED EMBODIMENTS

Figures 1, 2, 3:
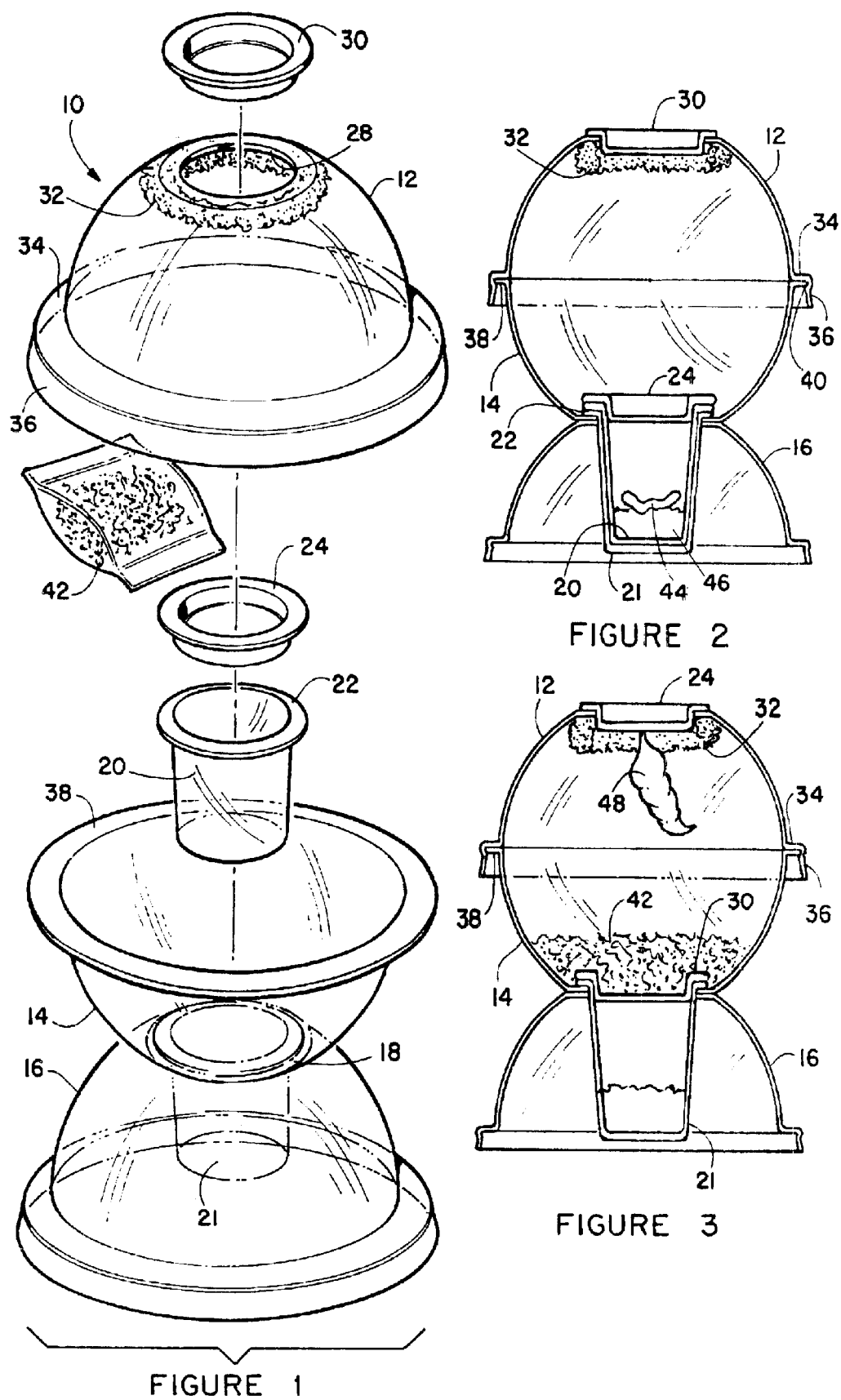
FIG. 1 is an exploded view of a first embodiment of the butterfly rearing kit.
FIG. 2 is an vertical section through the embodiment of FIG. 1 illustrating the larva housing arrangement.
FIG. 3 is a vertical section through the embodiment of FIG. 1 showing the chrysalis housing arrangement.

Referring to FIG. 1 there is seen an exploded view of a first embodiment of the butterfly rearing enclosure 10 of this invention. This embodiment is basically formed from three transparent plastic domes, an upper, removable, dome 12, a lower dome 14 and a base dome 16 permanently secured to the lower dome, by heat bonding, adhesive bonding, etc. A moderate temperature hot glue gun is convenient for bonding these domes 14 and 16 together. Domes 12, 14 and 16 may have any suitable concave shapes. While approximately hemispherical domes are preferred to provide maximum volume within the enclosure and optimum appearance, other curved shapes, truncated cones, cylinders, etc. may be used if desired. The domed lids provided on soft drinks of the sort that combine finely crushed ice and a liquid, like those sold under the "SLURPPY™" trademark, are often suitable for use as domes 12, 14 and 16.

Lower dome 14 and base dome 16 each have an opening 18 at the top of the dome. The hole edges are bonded together as seen. A small cup 21, similar to a conventional condiment cup for holding ketchup, mayonnaise, etc., is fastened, such as with hot glue, in opening 18. A flange 22 on cup 21 releasably supports the cup in opening 18 and may be adhesively bonded to domes 14 and 16 to further strengthen the structure.

A cup 20 for containing a larva, as detailed below, releaseably fits within cup 21. A conventional cap 24, of the sort supplied with condiment cups, fits snugly over the top of cup 20.

An opening 28 provided in the top of upper dome 12 is sized to receive a cap 30 identical with cap 24. A fibrous material such as cotton is secured, such as with hot glue or other adhesive, around opening 28 within upper dome 10.

Upper dome 12 has a base flange 34 and rim 36. Lower dome 14 has a base flange 38. Where soft drink lids are to be used, as mentioned above, lower dome 14 could be identical to upper dome 12, but with rim 36 trimmed away. Preferably, rim 36 has inwardly extending protrusion 40, which could be a series of small bumps, a circular central narrowing of rim 36, etc. This permits flange 38 to snap past protrusion 40 so that domes 12 and 14 are releasably connected together.

The enclosure kit preferably includes a package of fibrous material 42, such as dried moss, for use in the rearing process as described below. In addition a butterfly larva or chrysalis may be provided with the kit or supplied separately. Tape may also be provided for use in releasably holding lid 30 in place over opening 28 in upper dome 12.

In use, upper dome 12 is separated from lower dome 14 by popping flange 38 past protrusion 40. As seen in FIG. 2, a butterfly larva 44 (which appears to be a small caterpillar) may be in cup 20 when the kit is received. Otherwise, lid 24 is removed and a larva 44 is placed in cup 20. Preferably, a suitable quantity of conventional larva food 46 is placed in cup 20. Cup 20 may be removed from the enclosure for inspection and study of larva 44. After such inspection, cup 20 and lid 24 are replaced in base cup 21 and upper dome 12 is reconnected to lower dome 14.

After a period, typically one to three weeks, larva 44 will hang upside down from cap 24 and will shed its skin and form a chrysalis. Then cap 30 is removed, upper dome 12 is removed and cap 24 with chrysalis 48 hanging therefrom is placed in opening 28 in upper dome 12 and taped or otherwise fastened in place. Cap 30 is placed over cup 20, fibrous material 42 is spread over cap 30 as seen in FIG. 3 and the upper and lower domes 12 and 14 are brought back together.

If a second larva is to be reared, the larva is placed in another cup 20 before closing the enclosure. The old cup 20 is discarded or recycled.

After a period, typically 10–14 days, the chrysalis will turn dark and the butterfly's wings will begin to become visible. When the butterfly emerges, it will hang from the chrysalis shell or a fibrous material lining 32 surrounding opening 28. Its wings will be crumpled at this time. Over about 20 minutes, fluid will be pumped into the wings to expand them. Once the wings are filled, the butterfly will excrete excess fluid (meconium) which will be absorbed by fibrous material 42.

The butterfly will not eat for about two days, so it can be kept and observed for that period before release. If the butterfly is to be kept for a longer period, a cotton ball soaked in a sugar water solution may be placed in the enclosure. A freshly cut flower may also be placed in the enclosure, if desired.

A second embodiment of a butterfly rearing enclosure is illustrated in FIGS. 4 and 5. This enclosure 48 is intended for rearing a butterfly from the chrysalis state.

An upper dome 50 and a lower dome 52 are provided, essentially the same as domes 12 and 14 described above, but without base dome 16. The rim 55 and flange 57 dome connection is identical with that described above. Openings 51 and 53 are provided in upper and lower domes 50 and 52, respectively. A cap 54, generally similar to cap 24 as seen in FIG. 1 has a central area 56 surrounded by a rim 58 so that central area 56 will fit in opening 51 with rim 58 abutting upper dome 50 around opening 51. Cap 54 may be fastened to dome 50 with hot glue or other suitable adhesive. A fibrous material lining 60, such as cotton, is secured adjacent to the edge of opening 51 within upper dome 50 with hot glue or other suitable adhesive.

A closure member, typically a second cap 56, fits in opening 53 in lower dome 52 with a central area extending into the opening. Second cap 56 is bonded in place, typically with hot melt glue. A central hole 70 in cap 56 is provided to tightly receive a end of elongated rod 72 which is frictionally held in place but allows movement by overcome the frictional force. Rod 72 makes carrying the enclosure easy and can be supported by a vase, dirt in a flower pot, etc. Second cap 56 may be bonded to lower dome 52 with hot glue or other suitable adhesive. Similarly, rod 72 may be secured to closure member 64 with hot glue or the like if desired.

Enclosure 48 is generally received with a chrysalis 74 hanging from second cap 56 as shown in FIG. 5. The chrysalis may be adhesively bonded to the underside of cap. Preferably, a quantity of moss 76 or other suitable material is provided in lower dome 52. The chrysalis will transition to a butterfly as described above.

Other applications, variations and ramifications of this invention will occur to those skilled in the art upon reading this disclosure. Those are intended to be included within the scope of this invention, as defined in the appended claims.

We claim:

1. A butterfly rearing kit, which comprises:
   first and second concave transparent domes, each having an open base;
   connection means for releasably securing said open bases together to form an approximately spherical enclosure;
   openings in each of said first and second domes spaced from said open base;
   closure means for releasably closing said first dome opening; and
   support means connected to said second dome for supporting said enclosure with said first dome closure means approximately uppermost.

2. The butterfly rearing kit according to claim 1 wherein said connection means comprises first and second outwardly extending flanges adjacent to an open base of each of said first and second concave transparent domes, respectively, a rim on one of said first and second base flanges, said rim configured to have the other of said first and second base flanges fit inside said rim and further including means for releasably maintain said other open base flange within said rim.

3. The butterfly rearing kit according to claim 1 further including a quantity of fibrous material for placing in said second dome.

4. The butterfly rearing kit according to claim 1 wherein said closure means comprises a first cap having a raised center area for fitting within said opening in said first dome and an outwardly extending flange.

5. The butterfly rearing kit according to claim 1 wherein said support means comprises a third dome having a third opening conforming to said second opening, said second and third domes secured together with said second and third openings in alignment.

6. The butterfly rearing kit according to claim 5 further including a first cup bonded to edges of said aligned second and third openings, said cup including a flange for overlapping said aligned second and third openings, a second cup sized to nest in said first cup and a second cap sized to fit in either of said second cup and said first opening.

7. The butterfly rearing kit according to claim 1 further including a fibrous lining within said first dome secured around said opening.

8. The butterfly rearing kit according to claim 7 wherein said fibrous lining is a mass of cotton, said fibrous material is dry moss and further including a quantity of butterfly larva food in said second cup.

9. The butterfly rearing kit according to claim 1 wherein said support means comprises a third cap for closing said opening in said second dome, said third cap bonded to said second dome opening edge, a hole through said second cap and a rod sized to fit through said hole and be frictionally held by said hole.

10. A butterfly rearing kit, which comprises:

first and second concave transparent domes, each having an open base;

connection means for releasably securing said open bases together to form an approximately spherical enclosure;

first and second openings in each of said first and second domes, respectively, each spaced from said dome open bases;

first closure means for releasably closing said first dome opening;

second closure means for closing said second dome opening;

said second closure means bonded to edges of said second opening and extending across said second opening;

a hole through said second closure means;

a rod sized to fit through said hole and frictionally engage said hole;

attachment means on said first closure means for attachment of a chrysalis; and fibrous material secured inside said first dome adjacent to said first opening.

11. The butterfly rearing kit according to claim 10 wherein said connection means comprises first and second outwardly extending flanges adjacent to an open base of each of said first and second concave transparent domes, respectively, a rim on one of said first and second base flanges, said rim configured to have the other of said first and second base flanges fit inside said rim and further including means for releasably maintain said other open base flange within said rim.

12. The butterfly rearing kit according to claim 10 wherein said first and second closure means each comprises a cap having a central portion for extending through said first and second openings, respectively, and an outwardly extending flange for overlapping edges of said first and second openings.

13. The butterfly rearing kit according to claim 10 further including a quantity of fibrous material for placing in said second dome.

14. The butterfly rearing kit according to claim 10 wherein said attachment means is an adhesive for bonding a chrysalis to said first cap.

15. A butterfly rearing kit, which comprises:

first and second concave transparent domes, each having an open base;

connection means for releasably securing said open bases together to form an approximately spherical enclosure;

a support means comprising a third concave dome having an open base;

means for securing said second dome and third dome together in contact at locations spaced from said open bases of said second and third domes so that said enclosure is supported on a generally horizontal surface by said third dome;

a first opening in said first dome located so as to be generally uppermost when said enclosure is supported on said surface;

a second opening through said contact locations of said second and third domes;

said first and second openings having coextensive edges;

a first cup having an outwardly extending rim, said cup configured to fit in said second opening and be supported by said rim against said second opening edge;

means for bonding said first cup to said first and second opening coextensive edges;

a second cup sized to nest in said first cup;

first and second substantially similar caps configured to releasably close said first dome opening and said second cup, respectively;

an attachment surface on said second cap for attachment by a chrysalis in said second cup; and said first and second caps being interchangeable to permit said second cap to be removed with an attached chrysalis and replace said second cap so that said chrysalis can continue metamorphose in said enclosure.

16. The butterfly rearing kit according to claim 15 wherein said connection means comprises first and second outwardly extending flanges adjacent to an open base of each of said first and second concave transparent domes, respectively, a rim on one of said first and second base flanges, said rim configured to have the other of said first and second base flanges fit inside said rim and further including means for releasably maintain said other open base flange within said rim.

17. The butterfly rearing kit according to claim 15 further including a quantity of fibrous material for placing in said second dome.

18. The butterfly rearing kit according to claim 15 further including a fibrous material lining bonded to the interior of said first dome around said first opening.

19. The butterfly rearing kit according to claim 15 wherein said fibrous lining is cotton and said fibrous material is dry moss.

* * * * *